United States Patent [19]

Hautzel et al.

[11] Patent Number: 5,312,976
[45] Date of Patent: May 17, 1994

[54] PROCESS FOR THE PREPARATION OF 2-HYDROXY-NAPHTHALENE-6-CARBOXYLIC ACID

[75] Inventors: Volker Hautzel, Flörsheim am Main; Siegbert Rittner, Mörfelden-Walldorf, both of Fed. Rep. of Germany

[73] Assignee: Hoechst Aktiengesellschaft, Frankfurt am Main, Fed. Rep. of Germany

[21] Appl. No.: 917,049

[22] PCT Filed: Jan. 24, 1991

[86] PCT No.: PCT/EP91/00132
§ 371 Date: Jul. 31, 1992
§ 102(e) Date: Jul. 31, 1992

[87] PCT Pub. No.: WO91/11422
PCT Pub. Date: Aug. 8, 1991

[30] Foreign Application Priority Data

Feb. 2, 1990 [DE] Fed. Rep. of Germany ....... 4003043

[51] Int. Cl.⁵ ............................................. C07C 51/15
[52] U.S. Cl. ..................................................... 562/425
[58] Field of Search .......................................... 562/425

[56] References Cited

U.S. PATENT DOCUMENTS

| | | | |
|---|---|---|---|
| 1,593,816 | 7/1926 | Andre | 562/425 |
| 3,655,744 | 4/1972 | Yasuhara | 562/425 |
| 4,287,357 | 9/1981 | Mueller | 562/425 |
| 4,329,494 | 5/1982 | Montgomery | 562/425 |
| 4,345,095 | 8/1982 | Mueller | 562/425 |

OTHER PUBLICATIONS

Lindsey, Chem. Rev. 57, pp. 583–620 (1957).

Primary Examiner—Michael L. Shippen

[57] ABSTRACT

2-Hydroxy-naphthalene-6-carboxylic acid or its dipotassium salt is obtained in a good yield and purity without substantial formation of the isomeric compound 2-naphthol-3-carboxylic acid by reacting potassium β-naphtholate with potassium carbonate in the presence of carbon monoxide at a temperature above 260° C. in potassium formate as the solvent.

7 Claims, No Drawings

PROCESS FOR THE PREPARATION OF 2-HYDROXY-NAPHTHALENE-6-CARBOXYLIC ACID

The present invention relates to the technical field of intermediate products which can be employed, for example, for the synthesis of azo dyestuffs and polyester base materials.

2-Hydroxy-naphthalene-6-carboxylic acid is not only a useful synthesis unit for pharmaceuticals, textile auxiliaries and dyestuffs (cf., for example, European Patent Application Publication No. 0,292,955A), but in particular is also an important monomer for the preparation of liquid crystalline high-performance plastics and fibers having outstanding properties (cf. U.S. Pat. No. 4,393,191).

2-Hydroxy-naphthalene-6-carboxylic acid is synthesized industrially by a procedure analogous to the so-called Kolbe-Schmitt reaction, i.e. by reaction of the potassium salt of $\beta$-naphthol with carbon dioxide, under pressure at 200°-300° C. (cf., for example, U.S. Pat. Nos. 1,593,816, 4,329,494 and 4,287,357). However, the procedures described in these publications have some industrial disadvantages; considerable amounts of decomposition products, such as tars and resins, are formed which, like the 2-hydroxy-naphthalene-3-carboxylic acid and 2-hydroxy-naphthalene-3,6-dicarboxylic acid formed in side reactions, can be removed only with difficulty. Attempts have indeed been made to improve the reaction procedure and to reduce the formation of the intermediate products by the procedures described in European Patent Application Publications Nos. 0,053,824 and 0,081,753 by carrying out the process in a solvent, preferably kerosene. In spite of this advantage over the solvent-free Kolbe-Schmitt reaction, however, these two process variants still have the fundamental disadvantage that in each case 1 mol of $\beta$-naphthol remains unreacted in the reaction mass per mole of 2-hydroxy-naphthalene-6-carboxylic acid formed, which is why even in the best possible reaction procedure the yield is limited to a maximum of 50% in accordance with the equation:

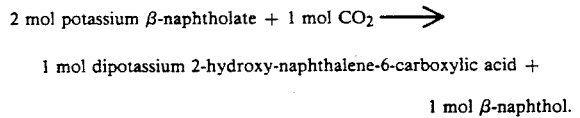

2 mol potassium $\beta$-naphtholate + 1 mol $CO_2$ ⟶

1 mol dipotassium 2-hydroxy-naphthalene-6-carboxylic acid +

1 mol $\beta$-naphthol.

In the preparation of the isomeric compound 2-hydroxy-naphthalene-3-carboxylic acid, it has already been proposed to avoid this disadvantage of incomplete conversion of the $\beta$-naphthol into naphtholcarboxylic acid by carrying out the reaction of potassium $\beta$-naphtholate with potassium carbonate in the presence of carbon monoxide in accordance with the equation:

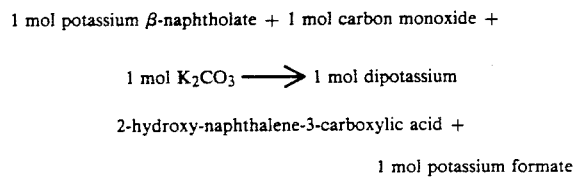

1 mol potassium $\beta$-naphtholate + 1 mol carbon monoxide +

1 mol $K_2CO_3$ ⟶ 1 mol dipotassium 2-hydroxy-naphthalene-3-carboxylic acid +

1 mol potassium formate (see British Patent Specification 1,155,776). However, if attempts are made to modify this procedure with the aim of preparing 2-hydroxy-naphthalene-6-carboxylic acid by varying the reaction conditions of temperature and carbon monoxide pressure, the synthesis of this 6-carboxy derivative remains unsuccessful.

It has now been found that 2-hydroxy-naphthalene6-carboxylic acid is obtained in a good yield and purity in a surprising manner if the reaction of the potassium $\beta$-naphtholate with potassium carbonate and carbon monoxide is carried out at a temperature above 260° C., such as at a temperature between 270° C. and 360° C., preferably between 280° and 320° C., and under a carbon monoxide pressure of above 10 bar, such as under a CO pressure of 50 to 150 bar, preferably between 70 and 140 bar, and in particular under a CO pressure between 80 and 120 bar, in potassium formate as the solvent (diluent).

The reaction according to the invention in potassium formate as the solvent or diluent (potassium formate melts above 167.5° C. to give a clear liquid) is carried out in accordance with the equation:

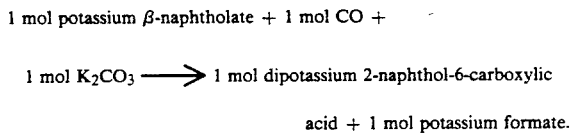

1 mol potassium $\beta$-naphtholate + 1 mol CO +

1 mol $K_2CO_3$ ⟶ 1 mol dipotassium 2-naphthol-6-carboxylic acid + 1 mol potassium formate.

The formate used as the solvent (diluent) is employed in at least the same molar amount as the potassium $\beta$-naphtholate starting substance; the amount of potassium formate used is not critical and can vary within wide limits. However, it is advantageous to employ a relatively large amount of potassium formate as the solvent (diluent), such as, for example, 2.5 to 18 times, preferably 6 to 15 times, the amount by weight of the potassium $\beta$-naphtholate employed, in order to ensure the best possible thorough mixing of the reactants potassium $\beta$-naphtholate and potassium carbonate, dissolved in the potassium formate, and the gaseous carbon monoxide at the phase boundaries. As with any reaction between a gas and a liquid phase to be carried out in industry, the customary good measures for thorough mixing are of course to be taken here, such as, for example, by using high-intensity stirrers, such as turbine stirrers.

The potassium formate employed as the solvent (diluent) not only has the effect of a high selectivity of the reaction to form the potassium salt of 2-hydroxy-naphthalene-6-carboxylic acid, but also has the advantage that it is not a foreign product in the reaction batch, but is identical to the by-product of the reaction. All of the potassium formate can therefore be employed again in later reactions, or carbon monoxide is obtained from the excess of this product by heating with concentrated sulfuric acid and can be recycled into a later reaction.

The potassium carbonate also employed in the procedure according to the invention is employed in the reaction in at least the same molar amount as the potassium $\beta$-naphtholate. The molar ratio between potassium $\beta$-naphtholate and potassium carbonate is as a rule between 1:1 and 1:1.5.

When the synthesis has ended, the batch can be worked up in various ways and the 2-naphthol-6-carboxylic acid formed can be isolated. One possibility is to dissolve the reaction product in water, to bring the pH to 7 with concentrated sulfuric acid and to filter off the unreacted $\beta$-naphthol which has precipitated. The filtrate is brought to a pH of 1 by means of sulfuric acid and the crude 2-hydroxy-naphthalene-6-carboxylic acid which has now precipitated is separated off. Fine purification is carried out by procedures analogous to known procedures, for example by redissolving under pressure in water or by purification with 1,4-dioxane (in this context cf., for example, German Offenlegungsschrift 3,800,989).

The following examples serve to illustrate the invention. The parts are parts by weight and the percentage data are percentages by weight, unless indicated otherwise. Parts by weight bear the same relation to parts by volume as the kilogram to the liter.

EXAMPLE 1

10 parts of potassium β-naphtholate, together with 7.6 parts of potassium carbonate and 75 parts of potassium formate, are introduced into a stainless steel autoclave provided with a stirrer, and the entire mixture is freed from residual moisture at 230° C. in the course of 5 hours, while stirring. Carbon monoxide is then passed in at room temperature under a pressure of 50 bar and the reaction is carried out under a carbon monoxide pressure of about 95 bar at 280° C. in the course of about 5 hours, while stirring intensively.

The reaction batch is then cooled, the autoclave is depressurized, the reaction product is dissolved in water, the pH is brought to 7 with concentrated sulfuric acid, the unreacted β-naphthol which has precipitated is filtered off, the filtrate is brought to a pH of 1 by means of sulfuric acid and the 2-hydroxy-naphthalene-6-carboxylic acid which has now precipitated is isolated. The 2-naphthol-6-carboxylic acid can be separated off from the by-products out of the crude product in the customary manner and can thus be obtained in a pure form.

Yield: 34% of theory, based on the β-naphthol as the starting substance.

The 2-naphthol-3-carboxylic acid is formed as a by-product to the extent of 5%.

EXAMPLE 2

The procedure is according to the procedure of Example 1, with the difference that the reaction is carried out at 300° C. using 125 parts of potassium formate. The 2-hydroxy-naphthalene-6-carboxylic acid is obtained in a yield of 40% of theory, in addition to 5.3% of 2-naphthol-3-carboxylic acid.

EXAMPLE 3

The procedure is according to the procedure described in the above examples under a carbon monoxide pressure of 100 bar and at a temperature of 320° C. over a period of about 5 hours, using 10 parts of potassium β-naphtholate, 7.6 parts of potassium carbonate and 75 parts of potassium formate. After working up the reaction mixture, 2-hydroxy-naphthalene-6-carboxylic acid is obtained in a yield of 37.5% of theory, in addition to 5.7% of 2-naphthol-3-carboxylic acid.

EXAMPLE 4

250 parts of potassium β-naphtholate, 190 parts of potassium carbonate and 3,500 parts of potassium formate are introduced into a stainless steel autoclave (about 5,000 parts by volume) provided with a disk stirrer, and the entire mixture is heated at 230° C. in the course of 5 hours, while stirring, for complete removal of the water (moisture) contained in the starting substances. Carbon monoxide is then introduced below the stirrer up to a pressure of 85 bar, the temperature of the batch is increased to 300° C. and the reaction is continued under a carbon monoxide pressure of about 100 bar for about a further 5 hours at a stirrer speed of about 1,100 revolutions/minute.

The reaction product is then worked up and purified by the procedure described in Example 1. The 2-hydroxy-naphthalene-6-carboxylic acid is obtained in a yield of 64% of theory.

We claim:

1. A process for the preparation of 2-hydroxy-naphthalene-6-carboxylic acid or its dipotassium salt, which comprises reacting potassium β-naphtholate with potassium carbonate and carbon monoxide at a temperature above 260° C. and under a carbon monoxide pressure above 10 bar in 2,5- to 18-times the amount by weight, calculated with respect to the amount of the potassium β-naphtholate, of potassium formate as the solvent or siluent, and optionally converting the dipotassium salt thus formed into 2-hydroxy-naphthalene-6-carboxylic acid.

2. The process as claimed in claim 1, wherein the reaction is carried out at a temperature between 280° and 320° C.

3. The process as claimed in claim 1, wherein the reaction is carried out under a carbon monoxide pressure between 70 to 140 bar.

4. The process as claimed in claim 2, wherein the reaction is carried out under a carbon monoxide pressure between 70 and 140 bar.

5. The process as claimed in claim 2, wherein the reaction is carried out under a carbon monoxide pressure between 80 and 120 bar.

6. The process as claimed in claim 1, wherein said dipotassium salt is the product of said process.

7. The process as claimed in claim 1, wherein said dipotassium salt is converted to 2-hydroxynaphthalene-6-carboxylic acid, so that 2-hydroxynaphthalene-6-carboxylic acid can be isolated as the product of said process.

* * * * *